United States Patent
Holt (12)

(10) Patent No.: US 6,333,038 B1
(45) Date of Patent: Dec. 25, 2001

(54) PROPHYLAXIS OF ALLERGIC DISEASE

(75) Inventor: Patrick G. Holt, Subiaco (AU)

(73) Assignee: TVW Telethon Institute for Child Health Research Princess Margaret Hospital for Children, Subiaco (AU)

( * ) Notice: Subject to any disclaimer, the term of this patent is extended or adjusted under 35 U.S.C. 154(b) by 0 days.

(21) Appl. No.: 08/663,125

(22) PCT Filed: Dec. 19, 1994

(86) PCT No.: PCT/AU94/00780

§ 371 Date: Aug. 26, 1996

§ 102(e) Date: Aug. 26, 1996

(87) PCT Pub. No.: WO95/17208

PCT Pub. Date: Jun. 29, 1995

(30) Foreign Application Priority Data

Dec. 22, 1993 (AU) .................................................. PM 3077

(51) Int. Cl.$^7$ .......................... A61K 39/35; A61K 39/36; A61K 39/39

(52) U.S. Cl. ..................................... 424/275.1; 424/278.1; 424/810; 424/812; 514/885

(58) Field of Search ............................ 424/195.1, 275.1, 424/812, 810, 278.1; 514/885

(56) References Cited

U.S. PATENT DOCUMENTS 5,216,132   6/1993   Basi ................................... 530/387.3

FOREIGN PATENT DOCUMENTS

| 0 058 021 | 8/1982 | (EP) . |
|---|---|---|
| 0 064 366 | 11/1982 | (EP) . |
| 0 083 497 | 7/1983 | (EP) . |
| 2 561 523 | 9/1985 | (FR) . |
| 89/10753 | 11/1989 | (WO) . |
| 93/10236 | 5/1993 | (WO) . |
| 96/13277 | 5/1996 | (WO) . |

OTHER PUBLICATIONS

R. S. Gieni et al., "Allergen–Specific Modulation of Cytokine Synthesis Patterns and IgE Responses in Vivo with Chemically Modified Allergen", Journal of Immunology, vol. 150, No. 1, Jan. (1993), pp. 302–310.
Dearman et al., "Inducible Interleukin–4–Secreting Cells Provoked in Mice During Chemical Sensitization", Database Biosis, Abstract No. 94:264762, Immunology, vol. 81, No. 4, (1994), pp. 551–557.
Romagnani et al., "Induction of $T_H1$ and $T_H2$ Responses: A Key Role for the 'Natural' Immune Response?", Immunology Today, vol. 13, No. 10, (1992), pp. 379–381.
J.R. Inglis et al., "The Regulation of Immune Responses to Dietary Protein Antigens", Immunology Today, vol. 8, 1987, pp. 93–98.

A. Miller et al., "Suppressor T Cells Generated by Oral Tolerization to Myelin Basic Protein Suppress Both in vitro and in vivo Immune Responses by the Release of Transforming Growth Factor β After Antigen–Specific Triggering", Proceedings of the National Academy of Sciences of the United States of America, vol. 89, No. 1, Jan. 1992, pp. 421–425.
Z. Zhang et al., "Orally Inducible Immune Unresponsiveness is Abrogated of IFN–γ Treatment[1]", The Journal of Immunology, vol. 144, No. 11, Jun. 1990, pp. 4163–4165.
P.G. Holt et al., "Suppression of IgE Responses Following Inhalation of Antigen", Immunology Today vol. 8, 1987., pp. 14–15.
P.G. Holt et al., "Defense Against Allergic Sensitization in the Healthy Lung: the Role of Inhalation Tolerance", Classical and Experimental Allergy, vol. 19, pp. 255–262.
C. McMenamin et al., "The Natural Immune Response to Inhaled Soluble Protein Antigens Involves Major Histocompatibility Complex (MHC) Class I–Restricted CD8 T Cell–Mediated but MHC Class II–Restricted CD4 T Cell–dependent Immune Deviation Resulting in Selective Suppression of Immunoglobulin E Production", The Journal of Experimental Medicine, vol. 178, No. 3, Sep. 1993, pp. 889–899.
P.G. Holt., "Primary Sensitisation to Inhalant Allergens during Infancy", Pediatric Allergy Immunology, vol. 1, 1990, pp. 3–13.
G. Hattevig et al., "Appearance of IgE Antibodies to Ingested and Inhaled Allergens during the First 12 Years of Life in Atopic and Non–Atopic Children", Pediatric Allergy and Immunology, vol. 4, Nov. 1993, No. 4, pp. 182–186.
Finkelman et al., "Lymphokine Control of in vivo Immunoglobulin Isotype Selection", Annual Review of Immunology, vol. 8, 1990, pp. 303–333.
J. Pene et al., "IgE Production by Normal B Cells Induced by Alloreactive T cell Clones is Mediated by IL–4 and Suppressed by IFN–γ", The Journal of Immunology, vol. 141, No. 4, Aug. 1988, pp. 1218–1224.
E.A. Wierenga et al., "Evidence for Compartmentalization of Functional Subsets of CD4 T Lymphocytes in Atopic Patients", The Journal of Immunology, vol. 144, No. 12, Jun. 1990, pp. 4651–4656.

(List continued on next page.)

Primary Examiner—Christopher R. Tate
Assistant Examiner—Janet W. Kerr
(74) Attorney, Agent, or Firm—Foley & Lardner

(57) ABSTRACT

The invention provides a method for preventing allergic disease in an individual susceptible to such disease, comprising administering an allergen to which the individual has not been sensitized previously. The allergen is administered in a dose and form effective to establish a stable population of allergen-specific T-helper-1-like memory lymphocytes capable of inhibiting activity or amplification of allergen-specific T-helper-2-like lymphocytes responsible for stimulating production of IgE antibodies specific for the allergen. Compositions for use in the method of the invention are also disclosed.

12 Claims, 5 Drawing Sheets

OTHER PUBLICATIONS

S. Romoagnani., "Induction of $T_H1$ and $T_H2$ Responses: a Key Role for the 'Natural' Immune Response?", Immunology Today, vol. 13, No. 10, Oct. 1992, pp. 379–426.

M.P. Chapman et al., "Purification and Characterization of the Major Allergen from Dermatophagoides Pteronyssinus–Antigen $P_1$", The Journal of Immunology, vol. 125, No. 2, Aug. 1980 pp. 587–592.

P.C. Fox et al., "IgE Antibody Suppression following Aerosol Exposure to Antigens", Immunology, vol. 43, No. 2, Jun. 1981, pp. 227–234.

G.A. Stewart et al., "Immunogenicity and Tolerogenicity of a Major House Dust Mite Allergen, Der p I from Dermatophagoides pteronyssinus, in Mice and Rats", Int. Archs. Allergy Appl. Immun., vol. 83, 1987, pp. 44–51.

T. Goodman et al., "Expression of the y–δT–cell Receptor on Intestinal CD8 Intraepithelial Lymphocytes", Nature, vol. 333, No. 6176, Jun. 1988, pp. 855–858.

R.T. Kubo et al., "Characterization of a Monoclonal Antibody which Detects all Murine αβ T Cell Receptors", The Journal of Immunology, vol. 142, No. 8, Apr. 1989, pp. 2736–2742.

C. McMenamin et al., "Regulation of T–Cell Sensitization at Epithelial Surfaces in the Respiratory Tract: Suppression of IgE Responses to Inhaled Antigens by CD3+ TcRα/βLymphocytes (putative) y/δT Cells)", Immunology, vol. 74, No. 2, Oct. 1991, pp. 234–239.

D.P. Dialynas et al., "Characterization of the Murine T Cell Surface Molecule, Designated L3T4, Identified by Monoclonal Antibody GK1.5: Similarity of L3T4 to the Human LEU–3/T4 Molecule", The Journal of Immunology, vol. 131, No. 5, Nov. 1983, pp. 2445–2451.

S.H.E. Kaufmann et al., "Crosstalk between α/β T Cells and y/δ T–Cells in vivo: Activation of α/β T–Cell Responses after y/δ T–Cell Modulation with the Monoclonal Antibody GL3", Proc. Natl. Acad. Sci., vol. 90 Oct. 1993, pp. 9620–9624.

S. Yamamoto et al., "Listeria Monocytogenes–Induced Gamma Interferon Secretion by Intestinal Intraepithelial y/δT Lymphocytes", Infection and Immunity, vol. 62, No. 5, May 1993, pp. 2154–2161.

I. Takagi et al., "Poly (Lactic/Glycolic Acid) Microspheres Containing Antigen as a Novel and Potential Agent of Immunotherapy for Allergic Disorders", Jpn. J. Allergol., vol. 41, No. 9, 1992, pp. 1388–1397.

Remington's Pharmaceutical Sciences, 16th Edition, Mack Publishing Co., PA, p. 40, 1980.

Morein et al., Nature, 308:457–460, 1984.*

Fundamental Immunology, Ed. by W.E. Paul, 3rd Edition, Raven Press, NY, NY, pp. 1327–1329, 1993.*

* cited by examiner

FIG. 5

| TREATMENT | CELLS | ANTIGEN CHALLENGE |
|---|---|---|
| NORMAL | — | AH/OVA |
| NORMAL | — | Der p1/AH |
| 1% OVA AEROSOL | UNFRACTIONATED ($10^6$ PER ANIMAL) | AH/OVA |
| 1% OVA AEROSOL | UNFRACTIONATED ($10^6$ PER ANIMAL) | Der p1/AH |
| 1% OVA AEROSOL | $\gamma\delta^+$ ($3 \times 10^4$ PER ANIMAL) | AH/OVA |
| 1% OVA AEROSOL | $\gamma\delta^+$ ($3 \times 10^4$ PER ANIMAL) | Der p1/AH |

$\log_2(\text{IgE, titer})$

PROPHYLAXIS OF ALLERGIC DISEASE

This application is the National Stage of International Application PCT/AU94/00780, filed Dec. 19, 1994.

This invention relates to methods and compositions for the prophylaxis of allergic disease, and in particular to allergic disease triggered by environmental antigens or allergens.

The present inventor has extensively reviewed the literature relating to induction of humoral and cellular immune responses to parenteral and enteral administration of allergens, and now proposes a novel and unexpected mechanism for inducing protective immunity against allergic diseases, via selective stimulation of allergen-specific T-helper-1 (TH-1) lymphocytes during early life.

For the purposes of this specification the following definitions are used:

allergen: any foreign antigen which stimulates allergic-type immune responses, characterised by activation of TH-2 lymphocytes and production of specific IgE antibody;

environmental allergen: any allergen found in the environment; such allergens are usually, but not necessarily, naturally occurring;

sensitisation: "priming" of populations of T-cells to respond specifically to subsequent challenge with the priming antigen or allergen; in the context of this specification, priming of allergen-specific TH-2 cells;

desensitisation: therapeutic administration of allergen, or a derivative thereof, to allergen-reactive "allergic" individuals, with the aim of selective suppression of the activity of allergen-specific T-cells, in particular TH-2 cells, and/or other cell types recruited into the allergen-specific immune or allergic response.

BACKGROUND OF THE INVENTION

It was recognised early in this century that feeding experimental animals an antigen they had previously not encountered elicited transient symptoms of immediate hypersensitivity, which waned with continued food antigen exposure, to be replaced by a state of antigen-specific unresponsiveness. The phenomenon is now known as Oral Tolerance, and has been shown to be preferentially directed against IgE-mediated immediate hypersensitivity responses and delayed-type hypersensitivity responses (1). This form of tolerance can be transferred from animal to animal by T-cells secreting TH-1-like cytokines (2,3), and allergen specific T-cells secreting such cytokines develop rapidly in the mesenteric lymph nodes during allergen feeding.(10,12)

The inventor was the first to recognise the equivalent phenomenon in the respiratory tract, and has been investigating the underlying mechanisms since the early 1980s (4,5). The essential elements are identical: repeated inhalation of antigen aerosols elicits an initially heterogenous immune response which includes a component of TH-2-dependent IgE production, but the latter eventually wanes in the face of repeated antigenic challenge, leaving only vestiges of specific IgG and IgA production. Animals passively exposed to antigen aerosols in this fashion are unable to mount subsequent IgE responses to the same antigen for the remainder of their lives, regardless of the route or intensity of challenge. As is the case with antigen feeding, the "tolerance" resulting from antigen inhalation is expressed preferentially against IgE and delayed-type hypersensitivity, and is mediated by T-cells, including a population expressing CD8, which secrete TH-1-like cytokines(6), Additionally, the option for this form of "tolerance" induction appears open to the immune system only at or around the time of initial allergen exposure—presensitised animals with stable on-going IgE responses are not "desensitised" by aerosol exposure(4,5).

These processes exhibit two further important features in common in experimental animals. Firstly, sensitivity to tolerance induction is genetically determined, and high sensitivity is co-inherited with the low-IgE-responder-phenotype. Operationally, this manifests as a requirement for up to $10^3$ to $10^4$-fold more intense allergen exposure to successfully tolerise high-IgE-responder rats and mice, compared to their low-responder counterparts. However, it is clear that both high and low responders can ultimately be tolerised by either route, and the inherent sluggishness of these mechanisms in the high-IgE-responders can be overcome by applying more intense allergen stimulation(4,5).

Secondly, the process functions poorly in the pre-weaning period(7), to the extent that allergen exposure in the very early phase of infancy can prime for subsequent pathogenic T-cell reactivity, as opposed to inducing protective tolerance: this is consistent with the existence of an early "window" of high risk for allergic sensitization, presumably due to delayed postnatal maturation of one or more key elements of mucosal immune function which are rate-limiting in the tolerance induction process(7).

It is not clear to what extent mucosal allergen exposure via the gastrointestinal tract can suppress ongoing TH-2 responses in IgE-positive high-responder animals, but recent work employing intranasally administered allergen peptides encourages further pursuit of this approach in the context of desensitisation.

Initial exposure of humans to ubiquitous environmental allergens occurs during infancy or early childhood, and the notion that many of the triggers for allergic disease in the adult are set during childhood is attracting increasing attention. In this context, there is a growing consensus, based upon an expanding paediatric sero-epidemiological literature, that high-level allergen. exposure during the first few months of life predisposes to allergic sensitisation (7), which manifests in later childhood as TH-2-like reactivity. This implies that, as in experimental animals, transient maturational defect(s) in aspects of immune function which are important for efficient "selection" for TH-1 reactivity to allergens encountered at mucosal surfaces may also be common in newborn humans.

The present inventor has now recognized that the key element of the relevant human literature, however, is the characteristic biphasic nature of IgE responses to individual food and inhalant allergens which commonly occur during early childhood.

Thus, both normal children and those with a family history of atopic responses typically develop serum IgE antibody responses against common food allergens during the first year of life, their magnitude and duration reflecting IgE-responder-phenotype(8). A comparable pattern is evident for IgE responses to inhalant allergens(8) (FIG. 1); however, the latter commence later in infancy, and take considerably longer to switch off ("tolerise") in the non-atopics. Furthermore, a much higher proportion of potential atopics maintain their serum IgE reactivity to inhalant allergens into later childhood than they do for food allergens (8).

These differences in the kinetics and overall efficiency of "tolerance" induction to inhalant versus dietary antigens may derive directly from the differing levels of antigen exposure in the two organs: as T-cell subset selection is "antigen driven", the less intense stimulation provided via low-level respiratory tract exposure may be expected to result in a slower and ultimately less efficient process.

It is known that the magnitude and duration of IgE responses to parenteral antigenic challenge in experimental animals is regulated by competing signals from $CD4^+$ T-cell subsets. In particular T-helper-2 (TH-2) cells, which secrete interleukin-4 and interleukin-5, promote IgE-B-cell switching, and TH-1 cells, which secrete interleukin-2 and interferon-γ, inhibit TH-2 clonal expansion and hence limit the IgE response (9) The present inventor's review of a variety of data obtained using in vitro experimental systems employing human peripheral blood T- and B-cells indicates that an identical mechanism exists in man(10), and this view is reinforced by the clear demonstration that both atopic and IgE-negative normal adults contain T-cells in peripheral blood which are reactive to the major inhalant allergens: in the atopic individuals, these cells appear to be predominantly of the TH-2 type, whereas in non-atopic individuals they appear to be mainly TH-1 (11) Considerable debate surrounds the precise classification of these human T-cell subsets relative to their murine counterparts, as respective cytokine patterns are not identical in the two species; accordingly, current opinion favours their classification in man as TH1-"like" and TH-2-"like" respectively.

Thus we suggest that in the non-atopic adult, each exposure to an environmental allergen would elicit a burst of TH-1-like cytokine release at sites of allergen presentation to the T-cell system, which would "protect" against the emergence of potentially pathogenic TH-2-like reactivity; each exposure event would additionally serve to consolidate host-protective TH-1-like "memory".

SUMMARY OF THE INVENTION

The present inventor now proposes that the T-lymphoid system in humans engages in active surveillance for environmental "allergens" throughout life, and that it is the nature of (as opposed to the mere presence of) allergen-specific T-cell responses in individuals that determines whether they express the allergic (atopic) or immunologically normal (non-responder) phenotype. The inventor has recognised that selection of the appropriate T-cell population is an antigen-driven process which occurs during the early stages of immune responses in the naive (unsensitised) host. If selection favours the growth of allergen-specific T-cells of the T-helper-1-like (TH-1)-like phenotype low-grade non-pathogenic IgG and IgA responses ensue, whereas the emergence of TH-2-like cells can lead to IgE production and eosinophilia and ultimately atopic disease. Additionally, TH-1-like cytokines actively suppress the expansion of TH-2-like clones, and hence a dominant, stable TH-1-like response to an allergen is proposed to be actively protective against the development of TH-2-like dependent allergic disease. With respect to T-cell responses to ubiquitous environmental allergens, the inventor's review of the recent paediatric literature has identified early childhood as the life period during which this selection normally occurs, and shows that the process can take several years to complete. Once the significance of the selection is appreciated, sufficient information is already known of how this natural selection process operates to contemplate controlling.it in vivo, via deliberate administration of allergen(s) in a form adapted to preferentially stimulate the development of host-protective TH-1-like immunity.

Our data suggest that "bystander" cell populations, in particular $CD8^+$ and/or $T_{\gamma/\delta}$ cells, can actively assist the overall TH-1-like selection process, and the term "TH-1-like immunity" in this specification is to be understood to include the contribution of these cells.

According to a first aspect, the invention provides a method of prevention of allergic disease in an individual susceptible to such disease, comprising the step of administering to a previously unsensitised individual a dose and form of allergen effective to induce establishment of a stable population of allergen-specific T-helper-1-like memory lymphocytes, said lymphocytes being capable of inhibiting activity or amplification of allergen-specific T-helper-2-like lymphocytes responsible for stimulating production of IgE antibodies specific for said allergen.

Preferably the allergen is an environmental antigen, and may be administered either singly or as a combination of two or more such allergens. The allergen may be in its naturally-occurring form. Alternatively the allergen may be a protein prepared using recombinant DNA technology, or may be a synthetic peptide. The allergen may be in purified form or may be impure or partially purified. The allergen may represent either the whole allergen molecule, or may be a part thereof, for example including one or more epitopes. Allergens contemplated to be suitable for use in the invention include those from house dust mite, animal danders such as cat, dog or bird dander, cockroach, grass pollens such as those from ryegrass or alternaria, tree pollens such as those from birch or cedar, feathers and moulds. The most suitable allergens will depend on the geographical location. For example, birch and cedar pollens are a major cause of allergies in northern Europe and Japan, but are of minor importance in Australia.

For both aspects of the invention, the allergen may be administered by the oral, intranasal, oronasal, rectal, intradermal, intramuscular or subcutaneous route. The adjuvant is preferably a liposome or a microbial cell wall product.

The allergen may optionally be administered together with an adjuvant. Suitable adjuvants will be known to the person skilled in the art. An adjuvant which selectively stimulates T-helper-1-like lymphocytes is preferred.

The dose of allergen will generally be in the nanogram to milligram range, depending on the allergen, the route of administration, and whether or not an adjuvant is used. The person skilled in the art will readily be able to determine the number and frequency of doses, using well-established principles. It is expected that for parenteral administration the dose range will be of the order of micrograms, that for intranasal administration the dose range will be in the microgram to milligram region, and that for oral or rectal administration the dose will be in the milligram to gram range. It will be appreciated that the dose could vary depending on whether an adjuvant is used, and depending on the nature of the adjuvant.

The method of the invention is suitable only for treatment of individuals who are not already allergic, i.e. hypersensitive, to the allergen being administered.

In general, the method is most suitable for treatment of children between 3 months and 7 years old, but is also applicable to individuals older than 7 years. Preferably the immunization is administered to children not less than 6 months old, more preferably not less than 9 months old.

Because in early childhood most individuals will not yet have been exposed to sensitisation by environmental allergens, it is considered that this period provides the optimum opportunity to select for allergen-specific host-protective TH-1-like mediated immunity. It is especially preferred that immunisation against airborne allergens, ie. allergens to which the individual is exposed by inhalation, be effected during early childhood.

According to one preferred embodiment of the invention, allergen is administered orally or intranasally during early childhood.

According to a particularly preferred embodiment, which is considered to provide selective induction of TH-1-like response to allergens with minimal stimulation of TH-2-like response, a mixture of two or more allergens of the airborne type is administered parenterally together with a TH-1-like selective adjuvant during early childhood.

According to a second aspect, the invention provides a sterile composition comprising an environmental allergen, together with an adjuvant capable of selectively stimulating T-helper-1-like lymphocytes, and optionally a pharmaceutically-acceptable carrier.

The allergen may be impure or purified, and may be of natural origin, produced by recombinant DNA technology, or synthetic.

Preferably the allergen is selected from the group which consists of house dust mite, animal danders such as cat, dog or bird dander, cockroach, grass pollens such as those from ryegrass or alternaria, tree pollens such as those from birch or cedar, feathers and moulds.

Preferably the composition is adapted for oral, intranasal, oronasal or rectal administration, but intradermal, subcutaneous or intramuscular administration may also be used.

BRIEF DESCRIPTION OF THE DRAWINGS

The invention will now be described in detail, with reference following non-limiting examples, and to the accompanying drawings, in which

FIG. 5 illustrates the antigen specificity of $\gamma\delta$ T cells in suppression of primal IgE responses. Asterisk, <controls; P<0.01.

DETAILED DESCRIPTION OF THE INVENTION

Without wishing to be bound by any mechanism for the observed beneficial effect, we propose that the "natural" mechanism for prevention of allergic sensitization in humans is a cognate immunological process, which operates as follows:

(i) during early childhood, there is active immunological recognition of the major environmental allergens which are encountered, and the maturing immue system mounts low-grade, initially heterogenous T-cell responses, comprising cross-competing TH-1-like and TH-2-like allergen-specific clones;

(ii) during repeated rounds of restimulation via normal environmental exposure, one of the competing T-cell phenotypes eventually becomes dominant in the response (typically TH-1-like in non-atopic normal subjects), leading to the establishment of a stable pool of T-memory cells which "police" immune responses to the allergen throughout later life, preventing the emergence of TH-2-like clones reactive against the same allergen.

Figure 1:
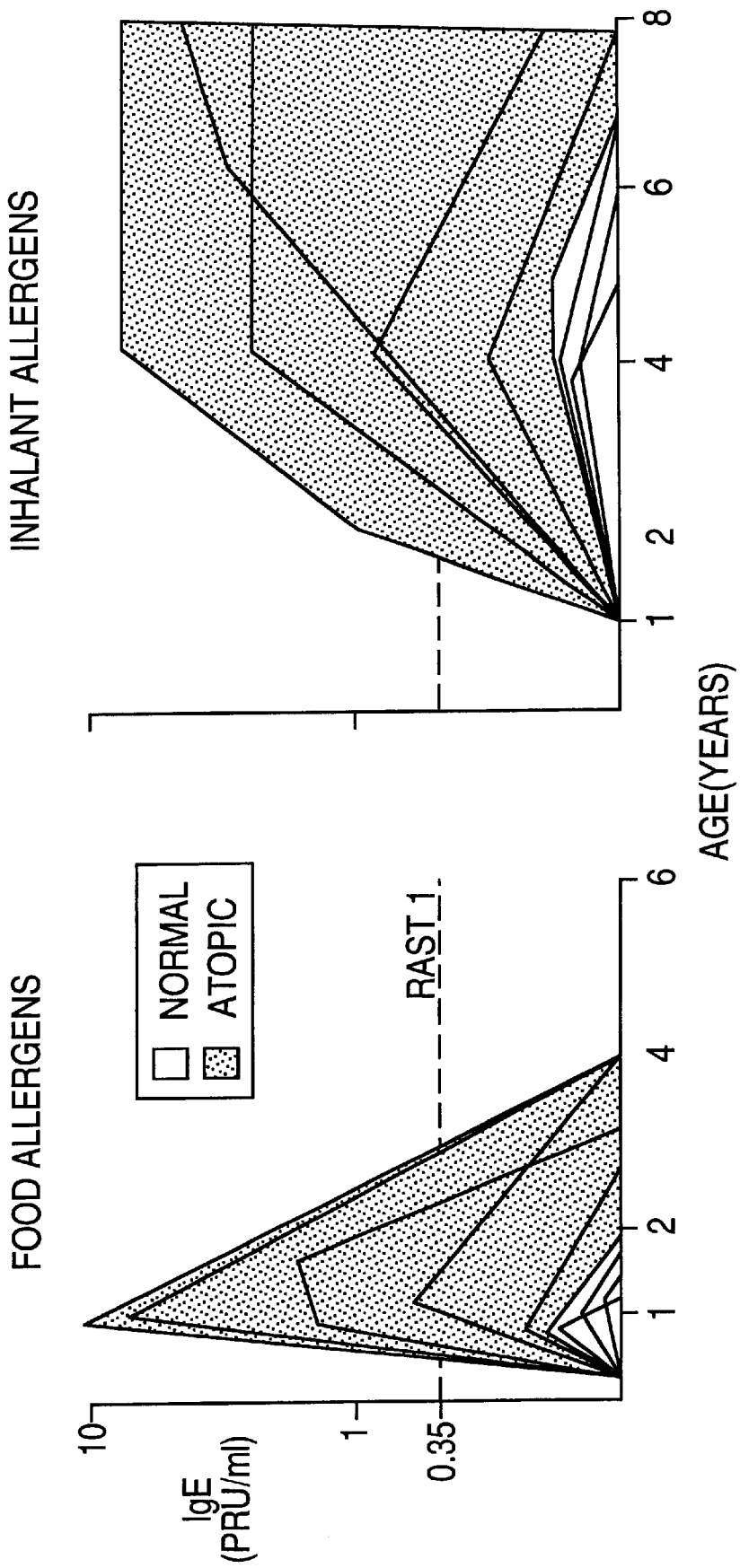
FIG. 1 illustrates post-natal serum IgE responses to environmental allergens in normal and atopic children. Individual curves represent results of repeated serum samples from a single child; curves for individual normal or atopic children fell within the regions shown. The data are derived from Reference 8. RAST represents radioallergoabsorbent test for IgE; PRU represents paper radioimmimoabsorbent test for IgE (units/ml).

With respect to inhalant allergens, this competition between co-existing antagonistic TH-1-like and TH-2-like T-cell populations appears to continue for a period of years during childhood, as these early allergen-specific IgE responses are often not terminated in non-atopics until as late as age 5–7 years(8); (FIG. 1). Based on current understanding of how T-cell reactivity develops, we consider that responses to inhalant allergens are "plastic" during this early period, and can be influenced toward either direction by exogenous factors. In particular, the known environmental risk factors for primary allergic sensitisation(7) must ultimately promote selection for TH-2-like reactivity. Additionally, the experimental literature indicates the existence of a series of powerful mechanisms which can potentially push the equilibrium of the immune system towards selection for host-protective anti-allergen responses, notably cytokines such as interleukin-12 and interferon-$\alpha$, produced by macrophages responding to certain microbial stimuli(12), and interferon-$\gamma$ produced by allergen-specific CD8$^+$ T-cells (6), both of which select strongly for TH-1-like cells by inhibiting the expansion of TH-2-like cells.

The inventor has now recognised that the plasticity of these early allergen-specific immune responses, and their slow kinetics in vivo, provide potential opportunities for intervention. The period of early childhood, which has long been designated as the "window for sensitisation" to environmental allergens, can thus equally be considered as providing a "window of opportunity" for regulating the development of normal anti-allergen immunity in as yet unsensitised children. Active intervention in the ongoing allergen-specific T-cell selection process which occurs during early childhood would optimise selection for allergen-specific host-protective TH-1-like immunity: the slow overall kinetics of the natural immune response to inhalant allergens (see FIG. 1) suggests that such an approach would be particularly applicable to prevention of sensitisation to such allergens.

Firstly, it is proposed to accelerate and control the natural selection process via either feeding or intranasal administration of allergen (or associated peptides) during early childhood. This approach derives from the finding that even in atopics, the success with which nature "tolerises" emerging IgE responses to food allergens during infancy is much higher than is achieved with inhalant allergens, where overall levels of allergenic stimulation are normally much lower. Thus enhancing the overall level of inhalant allergen stimulation via the right route at the right time may increase the overall efficiency of TH-1-like selection.

It is emphasized that while this approach may appear superficially similar to desensitisation strategies currently under development in many laboratories, it is in fact precisely the opposite: the latter are based upon usilencingf pathogenic TH-2-like cells in the sensitised host with pre-established TH-2-like memory, whereas the approach of the present invention is based on prevention of their emergence as a stable memory population in the first place.

A more direct strategy is suggested by recent developments in modern vaccine technology, which hold the promise of being able selectively to induce TH-1-like responses to nominal antigens via appropriate parenteral immunisation, with minimal danger of stimulating parallel TH-2-like pathways. Thus deliberate parenteral vaccination with a cocktail of the major inhalant allergens in appropriate TH-1-like selective adjuvant at the appropriate time in childhood may provide a safe and reliable method to bolster populations of appropriate TH-1-like cells which are emerging as a result of natural mucosal stimulation, thus hastening their eventual dominance of allergen-specific T-memory pools. With respect to inhalant allergens, the finding that a high proportion of serum IgE in most atopics can be accounted for by a relatively small number of major environmental allergen specificities(13) encourages the view that the relevant allergen (vaccine) cocktails may not necessarily be highly complex.

A preferred strategy is based on the use of adjuvants which:
a) stimulate the secretion of interleukin-12 and interferon-α by macrophages, thus selecting for the growth of TH-1-like cells by mechanisms described in Reference 12; these adjuvants are likely to be derived from microbial products; and/or
b) selectively stimulate an initial burst of Class 1 MHC-restricted immunity against the administered allergen, in order to select for the ensuing growth of allergen-specific TH-1-like cells by the mechanism which we have reported recently(6); a suitable adjuvant and delivery system for this purpose is expected to be various forms of liposomes, or an allergen-lipid conjugate, such as an iscom (an immune stimulating complex comprising *Quillaja saponis*, cholesterol, phospholipid and antigen).

EXAMPLE 1

Selective Suppression of Primary Allergen-Specific IgE Responses by Pre-Induction of Class 1 MHC-Restricted Immunity Mice were initially vaccinated against the allergen ovalbumin, using a protocol designed to prime CD8$^+$ T-cells. This protocol, which is known per se, is based upon selective activation of CD8$^+$ T-cells by initial priming with spleen cells which have been cytoplasmically "loaded" with soluble ovalbumin by osmotic shock. Our preliminary results indicate that the vaccinated mice are unable to mount subsequent high titre primary antigenovalbumin IgE response to parenteral challenge with ovalbumin, but are able to make normal IgG responses. This indicates that the initial vaccination selectively suppressed the TH-2-like component of the anti-ovalbumin response of these mice, whereas TH-1-like dependent IgG production proceeded normally. This result clearly supports the principles underlying the proposed vaccination strategy, and further experiments involving alternative vaccination protocols designed to achieve the same end result are in progress.

EXAMPLE 2

Use of Liposomes as Adjuvants

It has been suggested that liposomes can be used as vehicles for delivery of antigens in order to generate anti-viral immunity, in particular immunity based upon the generation of mixed "memory" in antigen-specific CD8$^+$ and CD4$^+$ TH-1-like viral antigen-specific T-cell populations. This strategy is being used for generation of allergen-specific CD8$^+$ TH-1-like immunity in mice, which is expected to be highly protective against the subsequent development of TH-2-like dependent IgE responses to these allergens. Various formulations of liposomes and allergens are being tested.

EXAMPLE 3

Microbial Cell Wall Products as Selected TH-1-Like Adjuvants

We and others have demonstrated that parenteral challenge of mice with certain microbial cell wall-derived adjuvants selectively suppresses TH-2-like dependent IgE responses, while stimulating TH-1-like dependent IgG responses. The most commonly available adjuvants, such as Freund's complete adjuvant, are not suitable for human use, is as they course tissue necrosis at the injection site. Cell wall extracts from a wide variety of bacterial strains are being tested in order to identify preparations which are both non-toxic and TH-2-like suppressive, using a screening protocol based on co-injection of extract together with ovalbumin into mice, and measuring the subsequent ovalbumin-specific IgE and IgG responses. A variety of cell wall-derived adjuvants from Mycobacterium tuberculosis, such as muramyl dipeptide, have been intensively investigated as potential adjuvants for human use, and it is contemplated that these may be useful for the purposes of this invention.

EXAMPLE 4

Use of a Modified Allergen as an IgE "Tolerogen"

Some recent publications have indicated that protein antigens artificially modified by the addition of conjugated lipid "tails" elicit Class I MHC-restricted immune responses, whereas the native proteins stimulate an exclusively Class II MCH-restricted response. As discussed above, according to the principles underlying the present invention such a modified antigen should also selected for TH-1-like immunity to the antigen, thus inhibiting the development of a TH-2-like dependent IgE response. Mice which had not been previously exposed to the allergen ovalbumin (OVA) were parenterally immunised and subsequently challenged with either native ovalbumin, or ovalbumin which had been structurally modified by conjugation with the lipid dodecenoic acid. Mice were initially primed with either native ovalbumin as a control, or with the lipid conjugate (Dodec-OVA) on Day 0, bled on Days 14 and 20, challenged with the same preparations respectively on Day 25, and bled again on Day 39. Serum titres of anti-ovalbumin IgE antibody were measured, and the results, presented as group median passive cutaneous anaphylaxis units, are shown in Table 1.

TABLE 1

|  | Ovalbumin | Dodec-OVA |
| --- | --- | --- |
| Day 14 | 1280 | <40 |
| Day 20 | 1280 | <40 |
| Day 39 | 1280 | <40 |

These results clearly show that priming with a modified antigen which selects for TH-1-like immunity does indeed prevent subsequent development of a TH-2-like dependent IgE response.

EXAMPLE 5

γδ T Cells Regulate IgE Responses to Inhale Allergen

We have previously shown that either oral or intranasal administration of allergen to animals which have not been previously exposed to this allergen can confer active protection against production of allergen-specific IgE by induction of a state of allergen-specific immunity which results in TH-1-like cytokine responses each time the allergen is encountered (6). Our earlier publication identified the cellular sources of these cytokines as being both Class I MHC-restricted $CD8^+$ T Cells and Class II MHC-restricted $CD4^+$ T cells.

We have now shown that allergen-specific T γδ cells provide a further source of TH-1-like cytokines in these responses; similar results have been obtained in both mice and rats.

C57BI/6J mice were exposed daily for 10 days to aerosolized OVA in phosphate-buffered saline and once weekly thereafter until used as described in our earlier work (8). Intraperitoneal (ip) challenge of a subgroup of these animals with 10 μg of OVA in 4.0 mg of aluminium hydroxide (AH) adjuvant revealed normal primary IgG responses but virtually complete suppression of parallel IgE responses, as demonstrated in our earlier studies (8). Splenocytes were prepared from other (unchallenged) "tolerant" animals and divided into three samples. The first sample was left unfractionated, the second was negatively depleted of $CD8^+$ cells by cytometry, and $CD8^+$ cells were purified from the third using positive selection by cytometry (Epics Elite, Coulter Electronics); the $CD8^+$ antibody used was from the 53-6.72 clone (14) and the cytometry methodology used was as previously described (7). The $CD8^+$ population was more than 99.5% pure, and the $CD8^-$ population contained less than 0.4% of contaminating $CD8^+$ cells. Immediately after ip injection of these cell populations, animals were immunised ip with 10 μg of OVA in 4.0 mg of AH adjuvant, and bled at Days 14 and 21.

IgG subclasses were measured by an enzyme-linked immunosorbent assay (ELISA) with anti-IgG subclass antibodies (Southern Biotechnology). Splenocytes were prepared as previously described and passed through nylon wool to remove adherent cells, thus yielding~85% T cells. Negative selection of αβ T cells was performed by flow cytometry with H57-597.19 (anti-αβ TCR) (15). γδ T cells constitute approximately 30% of the remaining cells; hence $1\times10^5$ splenocytes will contain $3\times10^4$ γδ T cells.

Figure 2:
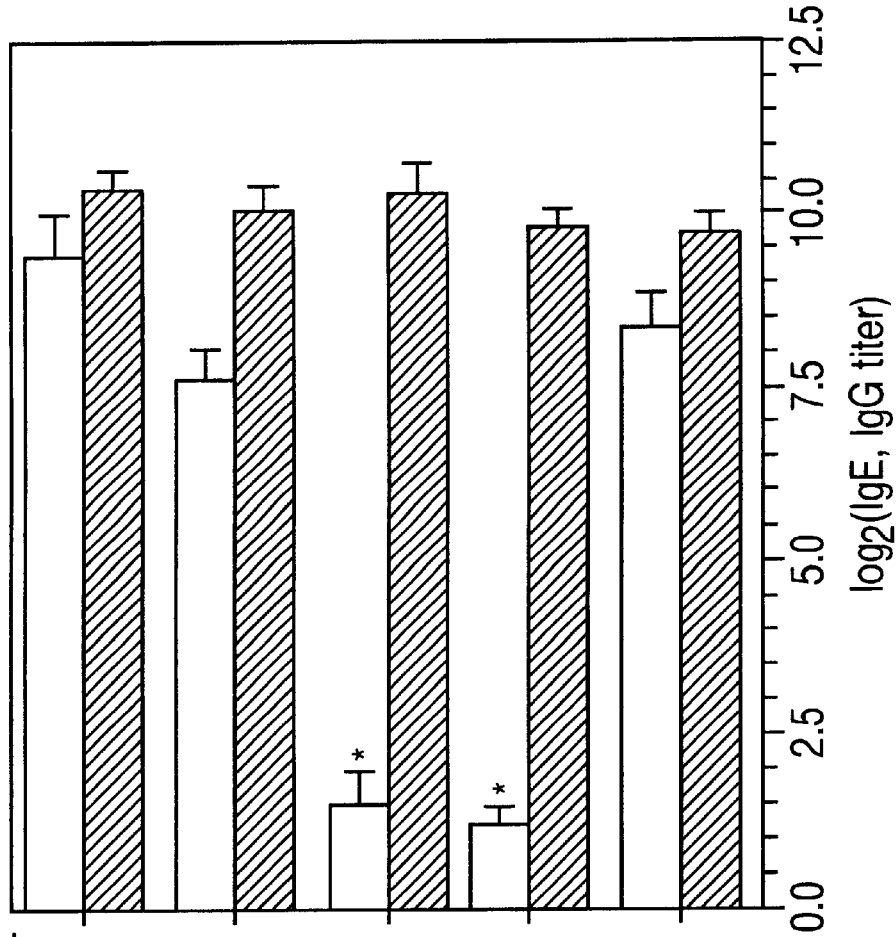
FIG. 2 shows selective suppression of IgE anti-ovalbumin (OVA) responses by adoptive transfer of CD8$^+$ lymphocytes from C57Bl/6J mice rendered "tolerant" to OVA by repeated exposure. Open bars, IgE; hatched bars, IgG (asterisk, <controls; P<0.01).

Adoptive transfer of $10^6$ unfractionated splenocytes from the tolerised mice inhibited IgE, but not IgG, antibody responses to ovalbumin in the recipient animals. These results are illustrated in FIG. 2.

The data shown are the mean±SD (n=5 to 10 per group) at Day 21 (peak primary Ig response) and indicate reciprocal log2 (IgE and IgG) anti-OVA titres as determined by standard methods (7). Data from Day 14 did not alter the interpretation of the results of these experiments.

The magnitude of the overall IgG anti-OVA response did not change significantly in mice pretreated with OVA aerosol. However, analysis of individual IgG subclasses by ELISA with subclass-specific anti-IgG antibodies (Southern Biotechnology) showed that suppression of the IgE response was accompanied by decreased $IgG_1$ reactivity and a compensatory rise in $IgG_{2a}$, whereas $IgG_{2b}$ and $IgG_3$ responsiveness was essentially unchanged.

EXAMPLE 6

Dose-Response Relationships for γδ T Cells

Figure 3:
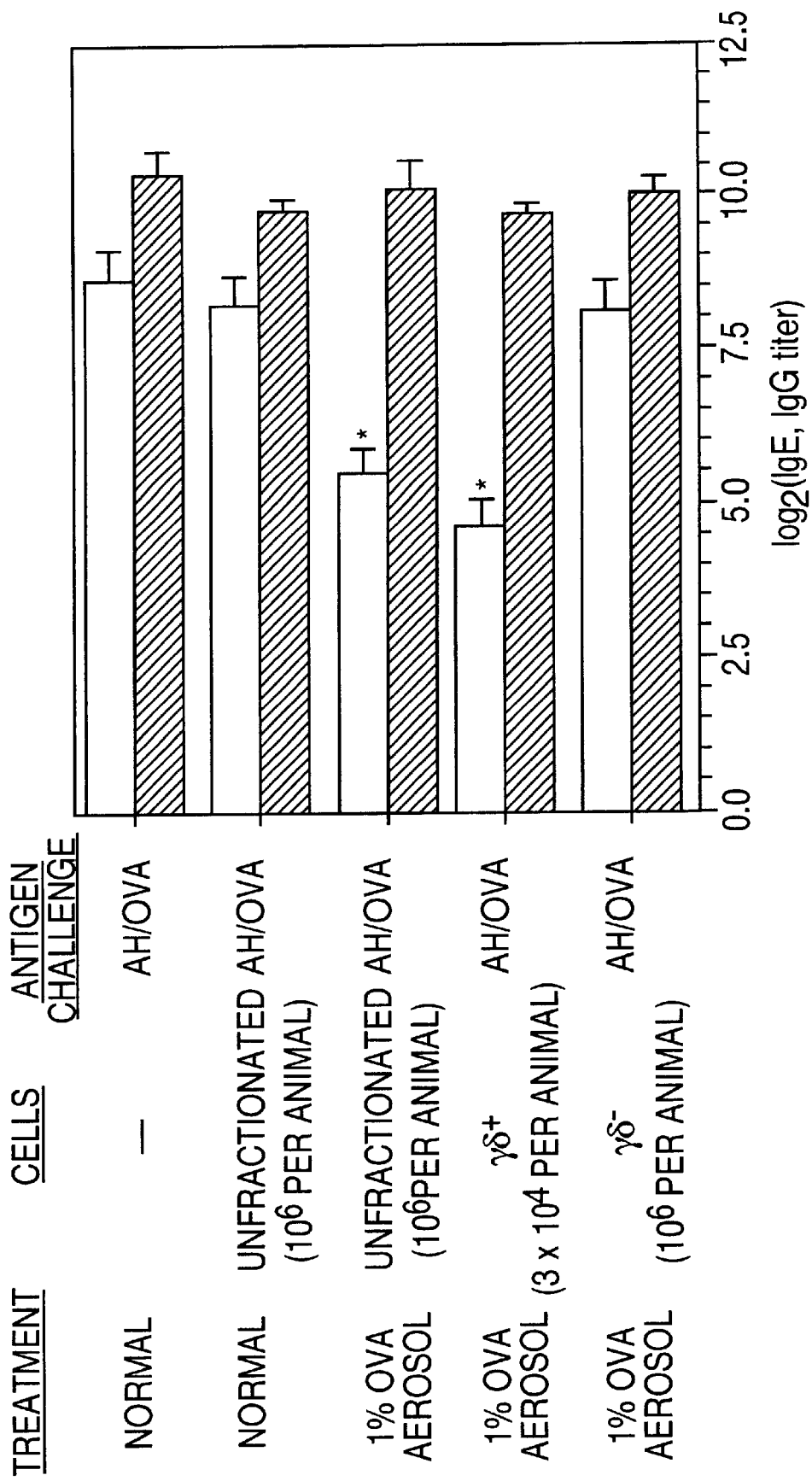
FIG. 3 illustrates suppression of IgE response by $\gamma\delta$ T cells. Open bars, IgE; hatched bars, IgG (asterisk, <controls; P<0.01).

Depletion of γδ$^+$ T cells abolished the capacity of splenocytes to suppress the IgG response. There are approximately $3\times10^4$ γδ T cells per $10^6$ splenocytes. When this number of γδ T cells purified to >98.5% by positive selection was transferred to recipient animals, the degree of suppression of the IgE response was comparable to that seen in animals receiving $10^6$ unfractionated cells. This is illustrated in FIG. 3. Spleen cells from tolerized animals were negatively depleted of γδ T cells with the antibody GL3 (16). GL3$^+$ (γδ$^+$) cells were prepared by positive selection. Adoptive transfer, ip antigen challenge, and determination of primary IgE and IgG responses were performed as above. These results are shown in FIG. 3.

Figure 4:
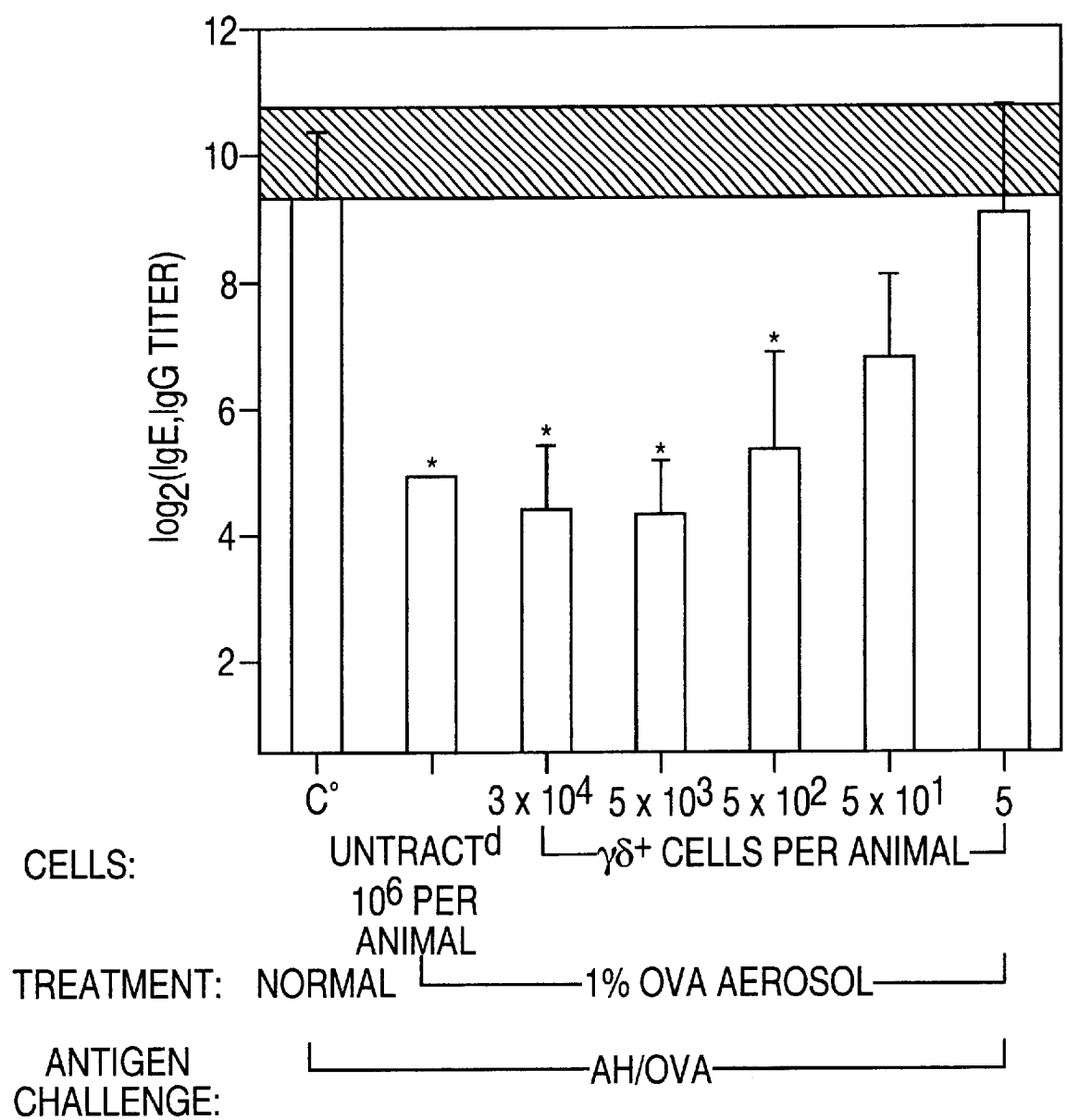
FIG. 4 shows dose-response analysis of adoptive transfer of OVA-specific tolerance by positively selected $\gamma\delta$ T cells from OVA-tolerant mice. Data shown are IgE titres from individual mice; the shaded area represents the 95% confidence limits for the peak primary IgG response in normal animals, and IgG titres in all animals in the experiment fell within this area. C*, comparable results obtained with untouched controls or recipients of splenocytes from naive animals. Asterisk, <controls; P<0.01.

Dose-response experiments showed that as few of $5\times10^2$ positively selected γδ T cells are sufficient for suppression of the IgE component of anti-OVA response. γδ T cells were prepared by negative selection from OVA-tolerant donors. Splenocytes were prepared as above and passed through nylon wool to remove adherent cells, yielding approximately 85% T cells. Negative selection of αβ cells was achieved by flow cytometry with H57-57.19 (anti-αβ TCR) (17). γδ T cells constitute approximately 30% of the remaining cells, so that $1\times10^5$ splenocytes will contain $3\times10^4$ γδ cells. These γδ cells yielded a suppression of the Igz response comparable to that achieved with positively selected cells, as shown in FIG. 4. We have previously shown that adoptive transfer of splenocytes depleted of αβ$^+$ T cells from OVA-tolerance rats was capable of mediating antigen-specific tolerant in the IgE isotype (17).

EXAMPLE 7

Antigen Specificity of γδ T Cell-Mediated Suppression

In order to test for the antigen specificity of the γδ T cell-mediated suppressive response, unfractionated splenocytes or purified γδ T cells were transferred from OVA-tolerant mice to groups of syngeneic recipients, which were then challenged with OVA or an unrelated antigen, Der P1 from the house dust mite. The transferred cells suppressed primary anti-OVA responses, but did not affect corresponding anti-Der P1 responses. Unfractionated or positively selected γδ T cells from OVA-tolerant rats were transferred, and the recipients were challenged with OVA or Der P1. The results are shown in FIG. 5. Antigen specificity was observed in this system, even at 50-fold higher cell dosages.

EXAMPLE 8

Cytokine Production in Mice Tolerised to OVA

Splenocytes from mice tolerized to OVA were challenged In vitro with 100 μg/ml OVA, and supernatants of these cells were harvested after 24 hrs for assessment of cytokine production. Splenocytes were depleted of >99.5% CD4$^+$, CD8$^+$ αβ$^+$ or γδ$^+$ T cells by negative selection, using flow cytometry. Cells were cultured at $2\times10^5$ per microplate well in RPMI medium containing $10^{-5}$ M 2-mercaptoethanol plus antibiotics, supplemented with 1 to 10% foetal calf serum, and stimulated with 100 μg/ml OVA. Supernatants were harvested after 24 hrs, and frozen at −20° C. prior to assay. IL-2 secretion was measured using a standard CTLL assay (6), and IFN-γ and transforming growth factor β1. TCF-β1 were determined by ELISA (Pharmingen and Genzyme respectively). The cells did not respond to an irrelevant control antigen, and cells from unimmunized control animals did not secrete detectable levels of cytokines in response to OVA.

Unfractionated splenocytes from tolerant animals secreted high levels of interferon-γ (IFN-γ) in response to specific antigen, and this secretory response was markedly reduced by depletion of CD8+ cells, but not CD4+ cells. Depletion of CD8+ cells markedly enhanced the OVA-specific interleukin-2 (IL-2) response. These results are summarized in Table 2, which shows mean ±standard deviation (SD) for replicate 24 hr culture supernatants.

TABLE 2

| Cells | Cytokine secretion | | |
|---|---|---|---|
| | IFN-γ (ng/ml) | IL-2 (U/ml) | TGF-β1 (ng/ml) |
| Unfractionated | 226.5 ± 7.8 | 2.7 ± 0.3 | 1.59 ± 0.15 |
| CD4− | 245.0 ± 28.3 | 1.8 ± 1.1 | 1.84 ± 0.73 |
| CD8− | 63.5 ± 12.0 | 9.3 ± 0.7 | 2.01 ± 0.57 |
| αβ− | 147.5 ± 21.9 | 2.6 ± 1.9 | 1.65 ± 0.39 |
| γδ− | 90.0 ± 2.5 | 8.7 ± 1.2 | 1.98 ± 0.24 |
| Non-T cells (CD3−) | ND | ND | 0.45 ± 0.09 |

ND: not determined.

TGF-β1 was also measured, since it has been suggested to play an important role in CD8+ T cell-mediated tolerance to orally-administered antigens (20). However, as shown in Table 1, TGF-β1 was in fact found to be produced in similar amounts by all T cell subsets after antigenic stimulation of tolerant animals, regardless of the potency of the subsets in transfer of tolerance. This suggests that TGF-β1 does not play a central role.

EXAMPLE 9

Proliferative Response to OVA of Splenic T Cells from Aerosol-Exposed Mice

We also examined the ability of splenic T cells to proliferate in vivo in response to OVA, following prior exposures of mice to OVA aerosols. The negative selection of αβT cells was performed as described above, and proliferation measured after stimulation with 100 μg/ml of OVA. Results, presented as mean ±SD of replicate cultures measured after 96 hrs incorporation of [$^3$H]-thymidine, are shown in Table 3. The subsets contained not more than 0.5% contaminant cells.

| Cell population | Proliferation ([$^3$H]DNA Synthesis) |
|---|---|
| Undepleted | 5,232 ± 75 |
| αβ− | 699 ± 32 |
| γδ− | 13,255 ± 563 |

Cells from OVA-exposed animals did not proliferate in response to an unrelated control antigen, and normal cells did not proliferate in the presence of OVA. A moderate proliferative response to antigen was consistently seen in unfractionated splenocytes; this was abrogated by depletion of αβ T cells, and enhanced by depletion of the γδ subset. As shown in Table 2, the latter procedure was also accompanied by a large increase IL-2 production. This suggests inhibition of αβ T cell proliferation by the γδ population, which is consistent with the reported effects of in vivo γδ T cell depletion (21).

We conclude that the effector cells mediating the selective suppression of IgE responses in this model in mice are CD4− CD8+ γδ+ T cells which are specific for OVA. From Table 1, it appears that these cells secrete interferon-γ in response to OVA, which is consistent with reports of γδ cell responses to stimulation with microbial antigens (22). They may also trigger interferon-γ release from other cell populations, such as natural killer cells, which are CD4−, or from CD8+ αβ T cells, both of which can be potent sources of interferon-γ (22). Thus the T cell response to inhaled OVA in tolerised mice displays a TH-1-like profile, which is consistent with the pattern of selective suppression of specific IgE and IgG$_1$ production and concomitantly enhanced IgG$_{2a}$ secretion observed in these animals. Our results suggest an important role for antigen-specific γδ T cells in the maintenance of immunological homeostasis in the lung and airways by selective suppression of potentially pathogenic TH-2-like dependent IgE responses, while preserving the host's capacity to produce specific IgG antibody.

EXAMPLE 10

Induction of Class I MHC-Restricted Immunity Against OVA Via Transfection

In order to gain more definitive evidence that immunisation which results in a selective boosting of CD8-mediated responses against allergens can confer protection against development of TH-2-like reactivity, we have primed for anti-OVA immunity via inoculation of mice with a cell line which expresses Class I but not Class II MHC responses, and which has been transfected with the gene encoding OVA. These cells produced OVA intracellularly, resulting in introduction of OVA into cytoplasmic Class I antigen-processing pathways, which are generally inaccessible to exogenous proteins. The transfected cells therefore present complexes of "processed" OVA or their surface in conjunction with Class I MHC antigens. This primes Class I MHC-restricted CD8+ T cells in the recipient animals for anti-OVA immunity. Primed animals and controls were then challenged parenterally with native OVA and bled 14 and 30 days later for determination of IgE anti-OVA titres. The results, presented as group medians in passive cutaneous anaphylaxis units, are shown in Table 4.

TABLE 4

| | Control | Primed |
|---|---|---|
| Day 14 | 640 | 40 |
| Day 30 | 640 | 40 |

OVA-specific reactivity was in fact demonstrated. These results are consistent with our overall postulate.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

1. Mowat, A. M.
    "The regulation of immune responses to dietary protein antigens"
    Imminol Today 1987 8 93–96.
2. Miller A., Lider O., Roberts A. B., Sporn, M. B.
    "Suppressor T cells generated by oral tolerization to myelin basic protein suppress both in vitro and in vivo immume responses by the release of TGF-β following antigenic specific triggering"

Proc Natl Acad Sci., USA, 1992 89 421–5.
3 Zhang Z., Michael J. G.
"Orally inducible immune unresponsiveness is abrogated by IFN-γ treatment"
J. Immunol., 1990 144 4163–5.
4 Holt, P. G and Sedgwick J. D.
"Suppression of IgE responses following antigen inhalation: A natural homeostatic mechanism which limits sensitization to aeroallergens"
Immmnol Today, 1987 8 14–5.
5 Holt, P. G. and McMenamin C.
"Defence against allergic sensitization in the healthy lung: the role of inhalation tolerance"
Clin. Exp. Allergy, 1989 19 255–62.
6 McMenamin, C. and Holt, P. G.
The natural immune response to inhaled soluble protein antigens involves major histocompatibility complex (MHC) class I-restricted $CD8^+$ T cell-mediated but MHC class II-restricted $CD4^+$ T cell-dependent immune deviation resulting in selective suppression of IgE production"
J. Exp. Med., 1993 178 889–99.
7 Holt, P. G, McMenamin, C. and Nelson, D.
"Primary sensitisation to inhalant allergens during infancy"
Ped. Allergy Imminol., 1990 1 3–13.
8 Hattevig, G., Kjellman, B. and Björkstén, B.
Appearance of IgE antibodies to ingested and inhaled allergens during the first 12 years of life in atopic and non-atopic children"
Ped. Allergy Immunol., 1993 4 182–6.
9 Finkelman, F. D., Holmes, J., Katona, I. M., Urban, J. J., Beckmann, M. P., Parkl L. S., Schooley, K. A., Coffman, R. L., Mosmann, T. R. and Paul, W. E.
"Lymphokine control of in vivo immunoglobulin isotype selection"
Annual Rev. Immunol., 1990 8 303–33.
10 Pene, J., Rousset, F., Briere, F., Chretien, I., Paliard, X., Banchereau, J., Spits, H. and De Vries, J. E.
"IgE production by normal human B cells induced by alloreactive T cell clones is mediated by IL-4 and suppressed by IFN-γ"
J. Immunol., 1988 141 1218–24.
11 Wierenga, E. A., Snoek, M., de Groot, C., Chretien, I., Bos, J. D., Jansen, H. M., Kapsenberg, M. L.
Evidence for compartmentalization of functional subsets of $CD2^+$ T lymphocytes in atopic patients.
J. Immunol., 1990 144 4651–6.
12 Romagnani, S.
"Induction of TH1 and TH2 responses: a key role for the "natural" immune response?"
Immunol. Today, 1992 13 379–81.
13 Chapman, M. D. and Platts-Mills, T. A. E.
"Purification and characterization of the major allergen from Dermatophagoides pteronyosinus-antigen $P_1$.
J. Immuol., 1980 125 587–92.

14 Fox, P. C. and Siraganian, R. P.
Immunology, 1981 43 227.
15 Stewart, G. A. and Holt, P. G.
Int. Arch. Allergy Appi. Immunol., 1987 83 44
16 Goodman, T. and Lefrancois, L.
Nature, 1988 333 855.
17 Kubo, R., Born, W., Kappler, P. and Pigeon, M.
J. Immunol., 1989 142 2236.
18 McMenamin, C. et al
Immunology, 1991 74 234.
19 Dialynas, D. P. et al
J. Immunol., 1983 131 2445.
20 Miller, A., Lider, O., Roberts, A. B. Sporn, M. B. and Weiner, H. L.
Proc. Natl. Acad. Sci. USA., 1992 89 421.
21 Kaufmann, S. H. E., Blum, C. and Yamamoto., S.
Proc. Natl. Acad. Sci. USA., 1993 90 9620.
22 Yamamoto., S. Russ, F., Teixeira, H., Conradt, P. and Kaufmann, S. H. E.
Infect. Immun., 1993 61 2154.

What is claimed is:

1. A method for the prophylactic treatment of allergic disease triggered by an environmental allergen in a human individual susceptible to such disease, comprising the step of administering to an individual who has not been sensitized by said environmental allergen a dose and form of said environmental allergen effective to induce establishment of a stable population of allergen-specific T-helper-1-like memory lymphocytes, said lymphocytes being capable of inhibiting activity or amplification of allergen-specific T-helper-2-like lymphocytes responsible for stimulating production of IgE antibodies specific for said environmental allergen.

2. A method according to claim 1, wherein the individual is 3 months to 7 yers old.

3. A method according to claim 2, wherein the individual is 6 months to 7 years old.

4. A method according to claim 3, wherein the individual is 9 months to 7 years old.

5. A method according to claim 1, wherein the allergen is administered together with an immunological adjuvant.

6. A method according to claim 5, wherein the adjuvant is one which selectively stimulates T-helper-1-like lymphocytes.

7. A method according to claim 1, wherein the environmental allergen is selected from the group consisting of insect allergens, pollens, animal danders, bird danders, feathers, and moulds.

8. A method according to claim 1, wherein the environmental allergen is an inhaled allergen.

9. A method according to claim 1, wherein two or more allergens are administered for the prophylactic treatment of allergic diseases triggered by said two or more allergens.

10. A method according to claim 1, wherein the environmental allergen is of biological origin.

11. A method according to claim 1, wherein the allergen is administered by the oral, intranasal, oronasal, rectal, intradermal, intramuscular or subcutaneous route.

12. A method according to claim 11, wherein the allergen is administered orally or intranasally.

* * * * *